(12) United States Patent
Holloway

(10) Patent No.: US 6,413,551 B1
(45) Date of Patent: Jul. 2, 2002

(54) TERMITICIDE COMPOSITION

(75) Inventor: David William Holloway, Toowoomba (AU)

(73) Assignee: Douglas Mervyn Gray (AU)

( * ) Notice: Subject to any disclaimer, the term of this patent is extended or adjusted under 35 U.S.C. 154(b) by 0 days.

(21) Appl. No.: 09/744,609

(22) PCT Filed: Jul. 29, 1999

(86) PCT No.: PCT/AU99/00610

§ 371 (c)(1),
(2), (4) Date: Jan. 26, 2001

(87) PCT Pub. No.: WO00/05963

PCT Pub. Date: Feb. 10, 2000

(30) Foreign Application Priority Data

Jul. 30, 1998 (AU) .............................................. PP 4931

(51) Int. Cl.$^7$ ........................ A01N 59/02; A01N 59/06; A01N 59/08; A01N 59/22; A01N 25/12

(52) U.S. Cl. ........................... 424/684; 424/40; 424/84; 424/623; 424/629; 424/647; 424/648; 424/677; 424/678; 424/679; 424/680; 424/681; 424/682; 424/684; 424/703; 424/705; 424/708; 424/713; 424/DIG. 11; 514/951

(58) Field of Search .......................... 424/84, 623, 647, 424/648, 682, 684, 705, 708, 713, DIG. 11, 40, 629, 703, 677–681; 514/951

(56) References Cited

U.S. PATENT DOCUMENTS 4,313,941 A * 2/1982 Duinker et al. ............. 514/144
5,332,580 A 7/1994 Young et al.
5,342,629 A 8/1994 Brown et al.

FOREIGN PATENT DOCUMENTS

EP 0 366 226 5/1990
WO WO 84/04230 11/1984

OTHER PUBLICATIONS

Derwent Abstracts, accession No. 1967–05901H, abstracting CH 465312 (1968).*
Chemical Abstracts 117:92497 (1992).*

* cited by examiner

Primary Examiner—John Pak
(74) Attorney, Agent, or Firm—Patton Boggs LLP

(57) ABSTRACT

A termiticide which comprises at least one compound which in the presence of a termite produces a termiticidally effective amount of hydrogen sulfide.

15 Claims, No Drawings

TERMITICIDE COMPOSITION

This application is a 371 of PCT/AU99/00610, filed on Jul. 29, 1999.

FIELD OF THE INVENTION

The present invention relates to a termiticide and method for the control of termites.

BACKGROUND OF THE INVENTION

There are many hundreds of commercially available termiticide chemicals and compositions. Many compositions are in liquid form which must be sprayed onto or about a termite nest. Other compositions are in powder form and include arsenic in the form of arsenious oxide. Each of these known termiticides must come into direct contact with a termite in order to kill the termite. However, termite nests are complex structures which include chambers linked by a complex system of tunnels. This means that it is very difficult and in practice virtually impossible to be able to deliver liquid or powdered agents to all parts of a termite nest. Further, not all termites access all parts of a nest. For example, workers do not enter the egg chambers. Thus, it is not possible to rely on termiticidal agents to be distributed to all areas of the nest by the termites themselves. The result of these difficulties is that under normal situations and using known agents it is not possible for all termites in a nest to be killed at one time. A termite nest can remain viable if only the queen and eggs survive, in which case a new colony can quickly breed. Thus in order to effectively kill a termite nest, repeat applications of the above known termiticides are required.

Other methods of termite control include providing a trap in which is housed an attractant and a poison. However, only those termites caught by the trap are killed and this method of control is not effective in killing an entire termite nest.

Insect and termite control by fumigation with active gaseous agents is also known. Whilst these methods of control may be able to expose more termites in a nest to the active agent as opposed to liquid spraying or dusting, fumigation has a number of disadvantages. First, fumigation is hazardous to the operator and also requires temporary evacuation of the site by personnel and domestic animals. Further, during fumigation, it is difficult to localize the active agent and prevent it from spreading into the environment.

An alternative to direct fumigation has been proposed for nematode control. Nematodes are parasitic worms which feed on plant roots. In this method, an aqueous thiocarbonate solution is sprayed onto or into nematode infected soil. Thiocarbonates are highly unstable and readily decompose on exposure to the soil to produce carbon disulfide. A disadvantage of these compounds is their instability and it is difficult to formulate storage stable solutions. These unstable thiocarbonates may be suitable for control of sedentary pests such as nematodes. However, such unstable compositions would be quite ineffective in the control of termites which are highly mobile and can travel large distances. The active agent would not remain viable in the environment for a sufficient period of time to allow any significant proportion of termites to com into contact with it.

OBJECT OF THE INVENTION

It is therefore an object of the present invention to provide a composition and method of termite control which may at least partially overcome the above disadvantages or provide the public with a useful choice.

According to a first broad form of the invention there is provided a termiticidal composition for the control or eradication of termites, the composition comprising a compound which in the presence of a termite produces a termiticidally effective amount of hydrogen sulfide.

The present invention is based upon the surprising discovery that a termiticidally effective amount of hydrogen sulfide may be generated in situ, the generation being catalyzed by the termites themselves. Although termites feed on cellulosic materials such as wood, they cannot ingest the wood directly. The termite must first at least partially digest the cellulose by exuding an acidic saliva. This saliva contains formic and acetic acids. Whilst not wishing to be bound by theory, it is believed that it is the acetic acid which is generated by the termites that is able to catalyse generation of the hydrogen sulfide.

Any chemical compound which generates hydrogen sulfide in the presence of a termite or under acidic conditions may be suitable for use in the present invention. Such compounds include sulfide materials and an especially preferred compound which readily decomposes to produce hydrogen sulfide in the presence of an acid is a blue dye known as ultramarine blue and which is believed to have the chemical formula $Na_7Al_6Si_6O_{24}S_2$.

Preferably, the termiticide of the present invention further includes a termite attractant. Termite attractants are known and typically comprise a carbohydrate food material. An especially preferred attractant is sugar. The termites typically collect the sugar, together with the hydrogen sulfide generating compound and return to the nest. Whilst not wishing to be bound by theory it is believed that when the termite returns to the nest, the acetic acid in the termite saliva reacts with the hydrogen sulfide generating compound to produce hydrogen sulfide. Because the termite nest is essentially a closed environment, the hydrogen sulfide remains in the nest and acts to kill the termites.

In some cases, the acid produced by the termites themselves may be insufficient to generate sufficient hydrogen sulfide to kill the entire nest. In a particularly preferred form of the invention, the termiticide includes a further agent which is able to undergo a chemical reaction which reduces the pH of the mixture. The chemical reaction may be initiated together with or after the initiation of hydrogen sulfide generation. This reduction in pH in turn is able to increase the rate and amount of hydrogen sulfide production such that more hydrogen sulfide is able to be generated than may be initiated by reaction of the hydrogen sulfide generating compound with the acetic acid. In this way, sufficient hydrogen sulfide may be generated to kill all the termites in the nest.

An example of a pH reducing agent is a compound which can be reduced by hydrogen sulfide to produce an acidic species. Examples of chemicals which may be reduced by hydrogen sulfide include ferric salts. A particularly preferred ferric salt is ferric chloride and in particular ferric chloride in the hexahdrate form. It is believed that the presence of water in the hexahydrate form facilitates the generation of acidic species.

The present inventor has also surprisingly observed that the generation of hydrogen sulfide may be increased if water is present. It is believed that the hydrogen sulfide dissolves in the water to form hydrosulphuric acid. The decrease in pH which occurs as a result of the formation of the hydrosulphuric acid promotes further hydrogen sulfide generation.

However, termite nests are generally a dry environment. Thus, in a preferred from of the present invention, the termiticide further includes an agent which in the presence of a termite and/or hydrogen sulfide can undergo chemical reaction in which a reaction product is water. This agent may be present in addition to or in place of the pH reducing agent. An especially preferred water producing agent is arsenious oxide. It is known that the following reaction can occur under acidic conditions, $$As_2O_3 + H_2S = As_2S_3 + H_2O,$$

and it is believed that this reaction may be occurring to produce at least some water. A further advantage of using arsenious oxide is that arsenious oxide is a known toxic agent which may facilitate killing the termites. Arsenious oxide has been traditionally used in the control of insects and termites and the like. Other preferred water producing agents include carbonates, sulfates, oxides and compounds of sodium and boron including their oxides and hydroxides. These other agents may be used in addition to or in place of arsenious oxide in instances where the use of the toxic arsenious oxide is undesirable.

The amount of water producing agent present may vary between about 1% to about 35 wt %. It will be appreciated that the amount of water producing agent necessary can depend on the amount of water in the environment to which the termiticide is applied and to whether the termiticide is applied internally or externally to the nest. For example, less water producing agents will be required if the environment contains a certain moisture level.

Generally, the termiticide of the present invention is applied to areas outside of the nest and typically the termites will carry the material on their bodies to the nest. In such cases, allowances must be made for the fact that not all the water producing agent (and other ingredients) will actually reach the nest.

Thus, generally a higher level of water producing agent (and other active agents) in the composition is required than when the composition is injected directly into the termite nest. In this case, the level of water producing agent may be as low as about 1%.

It can be seen that when a pH reducing reagent and/or water producing agent is present in the composition of the invention, only a small amount of acetic acid produced by a termite is required to initiate the generation of an effective amount of hydrogen sulfide.

The present inventor has also surprisingly discovered that when a termite comes into contact with a material which is irritating to the termite, the termite very quickly returns to the nest. Thus by including an irritant with the composition of the present invention, the termites may be encouraged to quickly return to the nest, and by doing so introducing the composition of the invention into the nest. When, in the nest, the generation of hydrogen sulfide may be initiated. Particularly preferred irritants are salts and a particularly preferred irritant is sodium chloride.

The composition of the present invention may also include other optional ingredients such as fillers, dilutents, flow modifiers, inhibitors, other termiticidal agents and the like. A particularly preferred filler is sulfur.

An especially preferred termiticide of the present invention comprises ultramarine, arsenious oxide, sodium chloride, sulfur and an attractant such as sugar. An especially preferred termiticide comprises about 2 to about 25 wt %, preferably about 5 to about 6 wt % ultramarine, about 10 to about 35 wt %, preferably 25 to 30 wt % arsenious oxide, about 4 to about 25 wt %, preferably about 7 to about 12 wt % sodium chloride, about 30 to about 80 wt %, preferably about 40 to about 60 wt % sulfur and an amount of an attractant sufficient to attract a termite. A further preferred termiticide of the present invention includes calcium carbonate in addition to or instead of arsenious oxide.

The termiticide of the present invention is preferably formulated such that it is in a powder form which enables it to be applied to the desired location by dusting.

According to a second broad form of the invention there is provided a method of controlling termites, the method comprising applying the termiticide of the first broad form to a termite nest or locus thereof.

Best Mode

A termiticide was prepared by combining and grinding 13 parts by volume ultramarine blue, 24 parts by volume arsenious oxide, 21 parts by volume sugar, 11 parts by volume sodium chloride and 51 parts by volume of sulfur.

The prepared composition was in the form of a powder. The powder was applied about a termite trail by dusting. This resulted in eradication of all termites in the termite nest. It was observed that only one application of the composition was necessary and there was no resurgence of the termite population in the killed nest.

The termiticide of the present invention does not kill a termite on contact as does many of the liquid termiticides which are currently commercially available. Thus, the termite is able to carry the termiticide back to the termite nest. When in the nest, the acetic acid generated by the termites is believed to decompose the ultramarine so as to produce hydrogen sulfide. Subsequent reaction of the hydrogen sulfide with arsenious oxide and/or carbonate is believed to generate water, which when combined with the hydrogen sulfide reduces the pH of the system. This reduction in pH initiates further decomposition of the ultramarine so as to produce hydrogen sulfide which is toxic to termites. Because the hydrogen sulfide is a gaseous agent it is able to spread throughout the nest such that effectively all termites and eggs in the nest are exposed. This complete exposure is not possible with traditional liquid or powdered reagents. Thus it will be appreciated that a single application of a preferred composition of the present invention is able to potentially kill an entire population of a termite nest.

Still further, because the hydrogen sulfide is generated in situ in the termite nest, only small amounts are required to be effective as compared to fumigation. Thus, the hydrogen sulfide is generated within the nest, the amount of hydrogen sulfide, if any, which escapes to the outside environment would typically be below a level which may be hazardous to persons or animals. Thus the termiticide of the present invention enables a highly toxic agent such as hydrogen sulfide to be delivered efficiently and safely. A further advantage of the preferred termiticide is that hydrogen sulfide is typically only generated in the termite nest. Under normal circumstances, the termiticide is substantially stable under ambient conditions.

In the present specification and claims, the word "comprising" and its derivatives including "comprises" and "comprise" include each of the stated integers but does not exclude the inclusion of one or more further integers.

It will be appreciated that various changes and modifications may be made to the embodiments described herein without departing from the spirit and scope of the invention.

What is claimed is:

1. A method for controlling termites which comprises contacting termites with a composition that includes at least one compound which in the presence of a termite produces a termiticidally effective amount of hydrogen sulphide.

2. The method of claim 1, wherein the compound is ultramarine.

3. The method of claim 2, wherein the compound is ultramarine blue.

4. The method of claim 2, wherein said composition further includes a compound, which in the presence of a termite and/or hydrogen sulphide, undergoes a chemical reaction in which a reaction product is water.

5. The method of claim 2, wherein said composition further includes arsenous oxide.

6. The method of claim 5, wherein said composition further includes a pH reducing agent.

7. The method of claim 5, wherein said composition further includes a termite attractant.

8. The method of claim 5, wherein said composition further includes a termite irritant.

9. The method of claim 1 wherein said composition comprises about 2–25 wt % of ultramarine blue, about 1% to about 35 wt % of arsenous oxide, and about 4% to about 25 wt % of sodium chloride.

10. The method of claim 1 wherein said composition comprises about 13 parts by volume ultramarine, about 24 parts by volume of arsenous oxide, about 21 parts by volume of sugar, about 11 parts by volume of sodium chloride, and about 51 parts by volume of sulphur.

11. The method of claim 1 comprising applying the composition in the vicinity of a termite nest.

12. A composition for controlling termites which produces a termiticidally effective amount of hydrogen sulphide, the composition comprising ultramarine, arsenous oxide and a termite irritant, whereby the termite irritant encourages the termite to return to the nest.

13. The composition of claim 12, comprising about 2–25 wt % of ultramarine blue, about 1% to about 35 wt % of arsenous oxide, and about 4% to about 25 wt % of sodium chloride.

14. The composition of claim 12 comprising about 13 parts by volume ultramarine, about 24 parts by volume of arsenous oxide, about 21 parts by volume of sugar, about 11 parts by volume of sodium chloride, and about 51 parts by volume of sulphur.

15. The composition of claim 14 which is in the form of a dusting powder.

* * * * *